United States Patent [19]

Loncrini et al.

[11] Patent Number: 4,496,576
[45] Date of Patent: Jan. 29, 1985

[54] COMPOSITIONS OF P-HYDROXYBENZOIC ACID ESTERS AND METHODS OF PREPARATION AND USE

[75] Inventors: Donald F. Loncrini, Ellisville; Thomas E. Haag, St. Louis County; Steven R. Freebersyser, Florissant, all of Mo.

[73] Assignee: Mallinckrodt, Inc., St. Louis, Mo.

[21] Appl. No.: 531,064

[22] Filed: Sep. 12, 1983

Related U.S. Application Data

[63] Continuation of Ser. No. 363,026, Mar. 29, 1982, abandoned, which is a continuation of Ser. No. 199,717, Oct. 23, 1980, abandoned.

[51] Int. Cl.³ .................. A01N 43/50; A01N 37/10
[52] U.S. Cl. .................................. 514/389; 514/543; 548/312
[58] Field of Search .......................... 424/237 R, 308; 548/312

[56] References Cited

U.S. PATENT DOCUMENTS 3,097,131  7/1963  Ueno et al. ........................... 424/308
3,960,745  6/1976  Billany et al. ........................ 424/326
3,987,184  10/1976  Foelsch ................................ 424/273
4,172,140  10/1979  Shull et al. ...................... 424/273 R

FOREIGN PATENT DOCUMENTS 1514469  6/1978  United Kingdom ................ 424/326

OTHER PUBLICATIONS

*Chemical Abstracts,* vol. 85, p. 86, (1976), Abst. No. 187144v.
Maeda et al., *Agr. Biol. Chem.,* 40(9), 1705–1709, (1976).

Primary Examiner—Delbert R. Phillips
Assistant Examiner—F. T. Moezie
Attorney, Agent, or Firm—Senniger, Powers, Leavitt and Roedel

[57] ABSTRACT

A composition having broad spectrum antimicrobial activity and being freeze and heat stable is comprised of a clear solution containing up to approximately 90% by weight of a eutectic mixture of three or more lower alkyl esters of p-hydroxybenzoic acid such as isopropyl p-hydroxybenzoate, isobutyl p-hydroxybenzoate and n-butyl p-hydroxybenzoate in a ratio between approximately 1:1:1 to 4:2:2, respectively, approximately 10% to 90% by weight of a "Glydant" solution (composed of 55% 1,3-bis(hydroxymethyl)-5,5-dimethylhydantoin and 45% water) and at least approximately 0.5% by weight based on the weight of the eutectic mixture and the "Glydant" solution of an anionic surfactant. The latter, for example, may be dioctyl sodium sulfosuccinate, sodium lauryl sulfate or the ammonium or sodium salt of sulfated nonylphenoxypoly(ethyleneoxy) ethanol.

36 Claims, No Drawings

COMPOSITIONS OF P-HYDROXYBENZOIC ACID ESTERS AND METHODS OF PREPARATION AND USE

This is a continuation of application Ser. No. 363,026, filed Mar. 29, 1982 which is a continuation of application Ser. No. 199,717 filed Oct. 23, 1980, both abandoned.

BACKGROUND OF THE INVENTION

This invention relates to compositions useful in effecting antimicrobial activity against various microorganisms and, more particularly, to novel compositions containing lower alkyl esters of p-hydroxybenzoic acid and which are in the form of clear solutions which exhibit advantageous properties and to methods of preparing and using such compositions.

Heretofore, it has been known that certain p-hydroxybenzoic acid alkyl esters such as isopropyl p-hydroxybenzoate, isobutyl p-hydroxybenzoate and n-butyl p-hydroxybenzoate are useful as antimicrobial agents or preservatives. Such p-hydroxybenzoic acid esters are usually solid at room temperature and have generally been used as crystals in the United States. Ueno U.S. Pat. No. 3,097,131 does disclose that eutectic mixtures of p-hydroxybenzoic acid alkyl esters may be emulsified in an aqueous solution containing such colloid protecting substances as gelatin, carboxymethyl cellulose and the like. However, it is not believed that such emulsions have the desired degree of heat stability or freeze stability for all applications and also may be subject to "breaking" or separating into two phases. Accordingly, it would be advantageous to formulate p-hydroxybenzoic acid alkyl esters into clear solutions which are both heat and freeze stable without the necessity of employing a stabilizing agent.

SUMMARY OF THE INVENTION

Among the several objects of the invention may be noted the provision of novel compositions of lower alkyl esters of p-hydroxybenzoic acid exhibiting broad spectrum antimicrobial activity; the provision of such compositions in the form of clear, colorless solutions; the provision of compositions of this type which remain liquid at temperatures down to −20° C. and are freeze and heat stable to 50° C.; and the provision of methods of preparing and using such compositions. Other objects and features will be in part apparent and in part pointed out hereinafter.

Briefly, the invention is directed to a composition having broad spectrum antimicrobial activity which comprises a clear solution containing up to approximately 90% by weight of a eutectic mixture of three or more lower alkyl esters of p-hydroxybenzoic acid, approximately 10% to 90% by weight of a solution containing approximately 55% of 1,3-bis(hydroxymethyl)-5,5-dimethylhydantoin and 45% of water, and at least approximately 0.5% by weight based on the weight of the eutectic mixture and the 1,3-bis(hydroxymethyl)-5,5-dimethylhydantoin solution of an anionic surfactant. The invention is also directed to the method of preparing such compositions and to the method of using such compositions to effect antimicrobial activity against a microorganism.

DESCRIPTION OF THE PREFERRED EMBODIMENTS

In accordance with the present invention, it has now been found that when a liquid eutectic mixture of three or more lower alkyl esters of p-hydroxybenzoic acid such as, for example, isopropyl p-hydroxybenzoate, isobutyl p-hydroxybenzoate and n-butyl p-hydroxybenzoate, is mixed with a solution containing approximately 55% of 1,3-bis(hydroxymethyl)-5,5-dimethylhydantoin and 45% of water in the presence of an anionic surfactant, no emulsion is formed but unexpectedly a clear, colorless solution or composition is formed which exhibits advantageous properties. Thus, we have found that such compositions do not freeze but remain liquid at temperatures down to −20° C. and are both freeze and heat stable (e.g., at 50° C.). In addition, these compositions are economical to prepare and use and are compatible with most formulations into which they are incorporated. Further, they exhibit broad spectrum antimicrobial activity against various microorganisms.

It is believed that the clear solutions or compositions of the invention are in the form of microemulsions which exhibit stability without containing a stabilizing agent.

The eutectic mixture component of our novel compositions may be any one of those whose preparation is described and claimed in the copending, coassigned application Ser. No. 199,719 of Donald F. Loncrini and John J. Taylor entitled Methods for Preparing Eutectic Mixtures of p-Hydroxybenzoic Acid Esters, now U.S. Pat. No. 4,309,564 dated Jan. 5, 1982. These eutectic mixtures are in the form of oils and are composed of three or more lower alkyl esters (i.e., alkyl groups containing 1 to 6 carbon atoms) of p-hydroxybenzoic acid such as isopropyl p-hydroxybenzoate, isobutyl p-hydroxybenzoate and n-butyl p-hydroxybenzoate in a ratio between approximately 1:1:1 and 4:2:2, preferably between 4:2.5:2.5 and 4:3:3. It will be understood that other eutectic mixtures of three or more lower alkyl esters of p-hydroxybenzoic acid such as a mixture of isopropyl p-hydroxybenzoate, sec-butyl p-hydroxybenzoate and amyl p-hydroxybenzoate, sec-butyl p-hydroxybenzoate, isobutyl p-hydroxybenzoate and n-butyl p-hydroxybenzoate, etc. may likewise be used in the practice of the invention. As disclosed in said application which is incorporated herein by reference, such eutectic mixtures are formed in situ preferably by first reacting p-hydroxybenzoic acid and a lower alkanol such as isopropyl alcohol in the presence of an esterification catalyst such as sulfuric acid to form a first lower alkyl ester of p-hydroxybenzoic acid (e.g., isopropyl p-hydroxybenzoate), reacting the resulting mixture with two or more lower alkanols (e.g., isobutyl alcohol and n-butyl alcohol) under heat to form a mixture of three or more lower alkyl esters of p-hydroxybenzoic acid (e.g., isopropyl p-hydroxybenzoate, isobutyl p-hydroxybenzoate and n-butyl p-hydroxybenzoate), quenching the reaction when the ratio of the respective lower alkyl esters of p-hydroxybenzoic acid to each other is such that the mixture thereof is liquid at room temperature, and isolating the resulting eutectic mixture. Other methods of forming such eutectic mixtures are also disclosed in the aforementioned application. These eutectic mixtures are thus formed directly without the necessity of forming and isolating the individual esters separately and then melting or otherwise blending them together to form liquid eutectic mixtures.

The second component of our novel compositions is a solution composed of 55% of 1,3-bis(hydroxymethyl)-5,5-dimethylhydantoin and 45% of water marketed under the trade designation "Glydant" by Glyco Chemicals, Inc. This product as marketed is a clear solution having a pH at 25° C. of 6.5–7.5 and a specific gravity of 1.1579±0.0026. It freezes at −20° C.

The anionic surfactants which, in combination with the "Glydant" solution, have been found useful to solubilize or microemulsify the above-referred-to eutectic oils or mixtures may be any suitable anionic surfactant such as, for example, dioctyl sodium sulfosuccinate, sodium lauryl sulfate and the ammonium or sodium salt of sulfated nonylphenoxypoly(ethyleneoxy) ethanol. The latter may be the ammonium salt of sulfated nonylphenoxypoly(ethyleneoxy) ethanol marketed under the trade designations "Alipal CO-436", "Alipal EP-110", "Alipal EP-115" or "Alipal EP-120" or the sodium salt of sulfated nonylphenoxypoly(ethyleneoxy) ethanol marketed under the trade designation "Alipal CO-433", all by GAF Corporation. Other anionic surfactants known to the art may also be used.

The amount of the eutectic oil or eutectic mixture which can be incorporated or solubilized into the compositions of the invention is dependent in part on which anionic surfactant is employed as well as on the amount of "Glydant" solution utilized. In general, up to approximately 90% by weight of the eutectic mixture may be solubilized in accordance with the practice of the invention using from approximately 10% to 90% by weight of the "Glydant" solution and at least 0.5% by weight of the anionic surfactant based on the weight of the eutectic mixture and the "Glydant" solution. More specifically, for example, approximately 90% of the eutectic mixture may be solubilized or microemulsified using 10% by weight of the "Glydant" solution and 6% by weight of dioctyl sodium sulfosuccinate based on the weight of the eutectic mixture and the "Glydant" solution, approximately 55% by weight of the eutectic mixture may be solubilized or microemulsified using 45% by weight of the "Glydant" solution and 7% by weight of sodium lauryl sulfate based on the weight of the eutectic mixture and the "Glydant" solution, and 40% by weight of the eutectic mixture may be solubilized or microemulsified using 60% by weight of the "Glydant" solution and 5% by weight of the ammonium salt of sulfated nonylphenoxypoly(ethyleneoxy) ethanol (marketed under the trade designation "Alipal CO-436") based on the weight of the eutectic mixture and the "Glydant" solution. In each instance, if it is desired to incorporate lesser amounts of the eutectic mixture, smaller amounts of the "Glydant" solution and the respective anionic surfactants are required. In most instances, approximately 2% to 10% by weight of the anionic surfactant component based on the weight of the eutectic mixture and the "Glydant" solution are used. Higher amounts of the anionic surfactant may be employed but are generally unnecessary.

As stated, the clear solutions or microemulsions of the invention possess broad spectrum antimicrobial activity and are effective against various microorganisms including bacteria, yeast and fungi as illustrated by the working examples set forth hereinafter. Moreover, as shown, the compositions of the invention are effective at concentrations as low as 32 ppm.

The following examples further illustrate the practice of the invention.

EXAMPLE 1

5 g of a eutectic mixture consisting of isopropyl p-hydroxybenzoate, isobutyl p-hydroxybenzoate and n-butyl p-hydroxybenzoate in a ratio of 4:2.3:2.4 was placed in a small test tube and heated to 70° C. 38.9 g of a solution marketed under the trade designation "Glydant" by Glyco Chemicals, Inc. (which is a solution composed of 55%, 1,3-bis(hydroxymethyl)-5,5-dimethylhydantoin and 45% water) were added to a 150-ml beaker containing 1 g of the ammonium salt of sulfonated nonylphenoxypoly(ethyleneoxy) ethanol marketed under the trade designation "Alipal CO-436" by GAF Corporation, mixed and heated to 45° C. in a water bath. The two solutions were added together and the resulting mixture was a clear, colorless solution which did not freeze at −20° C. The mixture remained stable at various temperatures. The mixture as constituted contained 11.1% by weight of the eutectic mixture and 86.6% by weight of the "Glydant" solution with the "Alipal CO-436" constituting 2.2% by weight based on the weight of the eutectic mixture and the "Glydant" solution.

EXAMPLE 2

Example 1 was repeated without using the anionic surfactant "Alipal CO-436". The resulting mixture was an opaque mixture with an oil layer at the top.

EXAMPLE 3

Example 1 was repeated using 9.3% sodium lauryl sulfate (marketed under the trade designation "Duponol C") instead of 2.2% "Alipal CO-436". This produced a clear, slightly yellow solution.

EXAMPLE 4

Example 3 was repeated using 2.2% sodium lauryl sulfate instead of 9.3%. This produced a clear solution.

EXAMPLE 5

Example 1 was repeated using 2.2% dioctyl sodium sulfosuccinate instead of 2.2% "Alipal CO-436". This produced a clear solution.

EXAMPLE 6

34.5 g of the "Glydant" solution (55% 1,3-bis(hydroxymethyl)-5,5-dimethylhydantoin) was placed in a 150-ml beaker containing 2.2% of the anionic surfactant "Alipal CO-436". The resulting mixture was heated to approximately 45° C. in a water bath and mixed well. 10 g of the eutectic mixture used in Example 1 was placed in a small test tube and heated to approximately 70° C. in a water bath. While the "Glydant"-"Alipal CO-436" mixture was being mixed on a magnetic stir plate, the eutectic mixture was added and the resultant mixture was further mixed for approximately 15 minutes. The resulting mixture was a clear solution.

EXAMPLE 7

Example 6 was repeated using 25.9 g of the "Glydant" solution, 2.1% dioctyl sodium sulfosuccinate and 20 g of the eutectic mixture. The resultant mixture was a clear solution.

EXAMPLE 8

Example 6 was repeated using 21.6 g of the "Glydant" solution, 2.1% dioctyl sodium sulfosuccinate and 25 g of the eutectic mixture. The resultant mixture was cloudy and yellowish in color. While mixing this mixture on a magnetic stir plate, an additional 2.1% dioctyl sodium sulfosuccinate was added making a total of 4.2% dioctyl sodium sulfosuccinate based upon the weight of the "Glydant" solution and the eutectic mixture. The resulting mixture was a clear solution.

EXAMPLE 9

Example 7 was repeated using 25.9 g water instead of 25.9 g of the "Glydant" solution. The resultant mixture was a white emulsion that split into two layers immediately.

EXAMPLE 10

Example 8 was repeated using 2.1% sodium lauryl sulfate instead of 2.1% dioctyl sodium sulfosuccinate. The resultant mixture was cloudy and yellowish in color. Upon the addition of another 2.1% sodium lauryl sulfate, a clear solution was obtained.

EXAMPLE 11

Example 6 was repeated using 4.3 g of the "Glydant" solution, 45 g of the eutectic mixture and 5.7% dioctyl sodium sulfosuccinate. A clear solution was formed.

EXAMPLE 12

Example 6 was repeated using 19.4 g of the "Glydant" solution, 27.5 g of the eutectic mixture and 6.9% sodium lauryl sulfate. A clear solution was formed.

EXAMPLE 13

Example 6 was repeated using 25.9 g of the "Glydant" solution, 20 g of the eutectic mixture and 5.1% "Alipal CO-436". A clear solution was formed.

EXAMPLE 14

The mixture or composition prepared as in Example 1 was tested to determine the minimum inhibitory concentration (MIC) of the composition against various microorganisms (i.e., bacteria, yeast and fungi) according to the following procedure:

(A) Agar plate preparation
(1) Tryptic Soy Agar (TSA) was prepared according to the manufacturer's directions by suspending 40 g TSA in cold deionized water (1 liter). The suspension was heated to boiling in order to dissolve completely and then autoclaved for 15 minutes at 15 pounds pressure at 121° C.
(2) After autoclaving, the media was cooled to 45° C. in a water bath.
(3) At this point, the mixture was aseptically added to the TSA at different levels in order to obtain the desired test concentrations.

(B) Inoculum
(1) The bacteria and yeast inoculum consisted of 0.1 ml of a 1:100 saline dilution of an overnight TSB broth culture (10-10 CFU/ml). CFU=Colony Forming Units.
(2) The fungus inoculum consisted of 0.1 ml of a spore-saline suspension harvested by gently rubbing the spores from a 1-week old Sabourand dextrose agar slant incubated at 25° C. with sterile saline (10-10 CFU/ml).
(3) A sterile Dacron swab was used to spread the inoculum evenly over the entire agar surface.

(C) Incubation
(1) The bacteria and yeast plates were incubated at 35° C. for 48 hours.
(2) The fungus plates were incubated at 30° C. for 72-96 hours.

(D) Recording of Results
0 = no growth
1+ = scant growth
2+ = moderate growth
3+ = heavy growth
4+ = confluent growth (same as control containing no preservative or antimicrobial agent)

The MIC is defined as the least concentration of the composition required to completely inhibit the growth of a microorganism.

The results were as follows:

| Microorganism | PPM | | | | | | | | Control | MIC |
| --- | --- | --- | --- | --- | --- | --- | --- | --- | --- | --- |
| | 2500 | 2000 | 1000 | 500 | 250 | 125 | 63 | 32 | | |
| Bacillus subtilis ATCC 6633 | 0 | 0 | 0 | 4+ | 4+ | 4+ | 4+ | 4+ | 4+ | 1000 |
| Staphylococcus aureus ATCC 6538 | 0 | 0 | 0 | 4+ | 4+ | 4+ | 4+ | 4+ | 4+ | 1000 |
| Staphylococcus epidermidis ATCC 1228 | 0 | 0 | 0 | 4+ | 4+ | 4+ | 4+ | 4+ | 4+ | 1000 |
| Streptococcus faecalis | 0 | 0 | 1+ | 4+ | 4+ | 4+ | 4+ | 4+ | 4+ | 2000 |
| Escherichia coli ATCC 8739 | 0 | 0 | 0 | 3+ | 4+ | 4+ | 4+ | 4+ | 4+ | 1000 |
| Klebsiella pneumoniae ATCC 8308 | 0 | 0 | 0 | 3+ | 4+ | 4+ | 4+ | 4+ | 4+ | 1000 |
| Salmonella typhosa ATCC 6539 | 0 | 0 | 0 | 0 | 1+ | 3+ | 4+ | 4+ | 4+ | 500 |
| Proteus vulgaris ATCC 13315 | 0 | 0 | 0 | 0 | 3+ | 4+ | 4+ | 4+ | 4+ | 500 |
| Serratia marcescens ATCC 8100 | 0 | 0 | 0 | 2+ | 4+ | 4+ | 4+ | 4+ | 4+ | 1000 |
| Enterobacter cloacae ATCC 23355 | 0 | 0 | 0 | 3+ | 4+ | 4+ | 4+ | 4+ | 4+ | 1000 |
| Pseudomonas aeruginosa ATCC 9027 | 0 | 0 | 1+ | 4+ | 4+ | 4+ | 4+ | 4+ | 4+ | 2000 |
| Pseudomonas aeruginosa ATCC 15442 | 0 | 0 | 0 | 4+ | 4+ | 4+ | 4+ | 4+ | 4+ | 1000 |
| Pseudomonas aeruginosa ATCC 13388 | 0 | 0 | 0 | 4+ | 4+ | 4+ | 4+ | 4+ | 4+ | 1000 |
| Pseudomonas aeruginosa ATCC 14502 | 0 | 0 | 1+ | 4+ | 4+ | 4+ | 4+ | 4+ | 4+ | 2000 |
| Pseudomonas stutzeri | 0 | 0 | 0 | 4+ | 4+ | 4+ | 4+ | 4+ | 4+ | 1000 |
| Candida albicans ATCC 10231 | 0 | 0 | 4+ | 4+ | 4+ | 4+ | 4+ | 4+ | 4+ | 2000 |
| Saccharomyces cerevisiae | 0 | 0 | 0 | 0 | 3+ | 4+ | 4+ | 4+ | 4+ | 500 |
| Aspergillus niger ATCC 9642 | 0 | 0 | 4+ | 4+ | 4+ | 4+ | 4+ | 4+ | 4+ | 2000 |
| Penicillium chrysogenum ATCC 9480 | 0 | 0 | 0 | 2+ | 3+ | 4+ | 4+ | 4+ | 4+ | 1000 |
| Trichophyton mentagrophytes | 0 | 0 | 0 | 0 | 2+ | 4+ | 4+ | 4+ | 4+ | 500 |

The minimum inhibitory concentration for the "Glydant" per se is as follows:

| Microorganism | MIC (ppm) |
| --- | --- |
| Bacillus subtilis ATCC 6633 | 500 |
| Staphylococcus aureus ATCC 6538 | 500 |
| Staphylococcus epidermidis ATCC 1228 | 500 |
| Streptococcus faecalis | 500 |
| Escherichia coli ATCC 8739 | 500 |
| Klebsiella pneumoniae ATCC 8308 | 500 |
| Salmonella typhosa ATCC 6539 | 250 |
| Proteus vulgaris ATCC 13315 | 250 |

| Microorganism | MIC (ppm) |
| --- | --- |
| Serratia marcescens ATCC 8100 | 500 |
| Enterobacter cloacae ATCC 23355 | 500 |
| Pseudomonas aeruginosa ATCC 9027 | 500 |
| Pseudomonas aeruginosa ATCC 15442 | 500 |
| Pseudomonas aeruginosa ATCC 13388 | 500 |
| Pseudomonas aeruginosa ATCC 14502 | 500 |
| Pseudomonas stutzeri | 500 |
| Candida albicans ATCC 10231 | 6000 |
| Saccharomyces cerevisiae | 250 |
| Aspergillus niger ATCC 9642 | 2000 |
| Pencillium chrysogenum ATCC 9480 | 4000 |
| Trichophyton mentagrophytes | 125 |

The minimum inhibitory concentrations for isopropyl p-hydroxybenzoate per se, isobutyl p-hydroxybenzoate per se and n-butyl p-hydroxybenzoate per ser are as follows:

| | Minimum Concentration for Inhibition (MIC), PPM | | |
| --- | --- | --- | --- |
| Microorganism | Isopropyl p-Hydroxybenzoate Water Solubility 0.08% | Isobutyl p-Hydroxybenzoate Water Solubility 0.02% | n-Butyl p-Hydroxybenzoate Water Solubility 0.015% |
| Bacillus subtilis ATCC 6633 | 500 | 250 | 250 |
| Staphylococcus aureus ATCC 6538 | 1000 | 250 | 125 |
| Staphylococcus epidermidis ATCC 1228 | 500 | 250 | 250 |
| Streptococcus faecalis | 1000 | 500 | 250 |
| Escherichia coli ATCC 8739 | 1000 | >1000 | 500 |
| Klebsiella pneumoniae ATCC 8308 | 500 | 500 | 250 |
| Salmonella typhosa ATCC 6539 | 1000 | 1000 | 500 |
| Proteus vulgaris ATCC 13315 | 500 | 250 | 125 |
| Serratia marcescens ATCC 8100 | 1000 | 1000 | 500 |
| Enterobacter cloacae ATCC 23355 | 1000 | 1000 | 250 |
| Pseudomonas aeruginosa ATCC 9027 | 2000 | >1000 | >6000 |
| Pseudomonas aeruginosa ATCC 15442 | >2000 | >1000 | >6000 |
| Pseudomonas aeruginosa ATCC 13388 | >2000 | >1000 | >6000 |
| Pseudomonas aeruginosa ATCC 14502 | >2000 | >1000 | >6000 |
| Pseudomonas stutzeri | 1000 | >1000 | 500 |
| Candida albicans ATCC 10231 | 250 | 125 | 125 |
| Saccharomyces cerevisiae | <125 | 125 | 32 |
| Aspergillus niger ATCC 9642 | 250 | 250 | 125 |
| Penicillium chrysogenum ATCC 9480 | <125 | 125 | 63 |
| Trichophyton mentagrophytes | <125 | 63 | 32 |

EXAMPLE 15

Example 14 was repeated using the final composition as prepared in Example 8.

Upon addition of the composition to the test media, oil beads of the eutectic mixture were formed. As the test media was mixed, the oil beads were broken up into smaller ones. The test media was mixed for several minutes and poured into the plates just prior to solidification. After the plates were poured, all plates including the one containing a concentration of 32 ppm had visible oil beads, with the amount present decreasing as the concentration decreased.

The results of the determination of MIC activity are as follows:

| Microorganism | PPM | | | | | | | Control | MIC |
| --- | --- | --- | --- | --- | --- | --- | --- | --- | --- |
| | 2000 | 1000 | 500 | 250 | 125 | 63 | 32 | | |
| Bacillus subtilis ATCC 6633 | 0 | 0 | 0 | 1+ | 3+ | 4+ | 4+ | 4+ | 500 |
| Staphylococcus aureus ATCC 65380 | 0 | 0 | 0 | ?+ | 4+ | 4+ | 4+ | 4+ | 500 |
| Staphylococcus epidermidis ATCC 12280 | 0 | 0 | 0 | 3+ | 4+ | 4+ | 4+ | 4+ | 500 |
| Streptococcus faecalis | 0 | 0 | 0 | 3+ | 4+ | 4+ | 4+ | 4+ | 500 |
| Escherichia coli ATCC 8739 | 0 | 0 | 4+ | 4+ | 4+ | 4+ | 4+ | 4+ | 1000 |
| Klebsiella pneumoniae ATCC 8308 | 0 | 0 | 0 | 4+ | 4+ | 4+ | 4+ | 4+ | 500 |
| Salmonella typhosa ATCC 6539 | 0 | 0 | 0 | 2+ | 4+ | 4+ | 4+ | 4+ | 500 |
| Proteus vulgaris ATCC 13315 | 0 | 0 | 0 | 4+ | 4+ | 4+ | 4+ | 4+ | 500 |
| Serratia marcescens ATCC 8100 | 0 | 0 | 3+ | 4+ | 4+ | 4+ | 4+ | 4+ | 1000 |
| Enterobacter cloacae ATCC 23355 | 0 | 0 | 3+ | 4+ | 4+ | 4+ | 4+ | 4+ | 1000 |
| Pseudomonas aeruginosa ATCC 9027 | 0 | 1+ | 4+ | 4+ | 4+ | 4+ | 4+ | 4+ | 2000 |
| Pseudomonas aeruginosa ATCC 15442 | 0 | 3+ | 4+ | 4+ | 4+ | 4+ | 4+ | 4+ | 2000 |
| Pseudomonas aeruginosa ATCC 13388 | 0 | 0 | 4+ | 4+ | 4+ | 4+ | 4+ | 4+ | 2000 |
| Pseudomonas aeruginosa ATCC 14502 | 0 | 1+ | 4+ | 4+ | 4+ | 4+ | 4+ | 4+ | 2000 |
| Pseudomonas stutzeri | 0 | 0 | 3+ | 4+ | 4+ | 4+ | 4+ | 4+ | 1000 |
| Candida albicans ATCC 10231 | 0 | 0 | 0 | 0 | 4+ | 4+ | 4+ | 4+ | 250 |
| Saccharomyces cerevisiae | 0 | 0 | 0 | 0 | 0 | 0 | 1+ | 4+ | 63 |
| Aspergillus niger ATCC 9642 | 0 | 0 | 0 | 1+ | 3+ | 4+ | 4+ | 4+ | 500 |
| Penicillium chrysogenum ATCC 9480 | 0 | 0 | 0 | 0 | 0 | 0 | 0 | 4+ | <32 |
| Trichophyton mentagrophytes | 0 | 0 | 0 | 0 | 0 | 0 | 0 | 4+ | <32 |

EXAMPLE 16

Example 14 was repeated using the final composition as prepared in Example 8 containing 10% dioctyl sodium sulfosuccinate based upon the weight of the "Glydant" solution and the eutectic mixture.

Upon addition of the composition to the test media and pouring of the resultant mixture into the plates, oil beads were present in those plates containing a concentration of 2000, 1000 and 500 ppm. At concentrations below 500 ppm, oil beads were not visible to the naked eye.

The results of the determination of MIC activity are as follows:

| Microorganism | PPM | | | | | | | Control | MIC |
|---|---|---|---|---|---|---|---|---|---|
| | 2000 | 1000 | 500 | 250 | 125 | 63 | 32 | | |
| *Bacillus subtilis* ATCC 6633 | 0 | 0 | 0 | 0 | 0 | 4+ | 4+ | 4+ | 125 |
| *Staphylococcus aureus* ATCC 65380 | 0 | 0 | 0 | 0 | 1+ | 4+ | 4+ | 4+ | 250 |
| *Staphylococcus epidermidis* ATCC 12280 | 0 | 0 | 0 | 0 | 1+ | 4+ | 4+ | 4+ | 250 |
| *Streptococcus faecalis* | 0 | 0 | 0 | 0 | 4+ | 4+ | 4+ | 4+ | 250 |
| *Escherichia coli* ATCC 8739 | 0 | 0 | 2+ | 4+ | 4+ | 4+ | 4+ | 4+ | 1000 |
| *Klebsiella pneumoniae* ATCC 8308 | 0 | 0 | 0 | 0 | 4+ | 4+ | 4+ | 4+ | 250 |
| *Salmonella typhosa* ATCC 6539 | 0 | 0 | 0 | 0 | 4+ | 4+ | 4+ | 4+ | 250 |
| *Proteus vulgaris* ATCC 13315 | 0 | 0 | 0 | 0 | 3+ | 4+ | 4+ | 4+ | 250 |
| *Serratia marcescens* ATCC 8100 | 0 | 0 | 1+ | 3+ | 4+ | 4+ | 4+ | 4+ | 1000 |
| *Enterobacter cloacae* ATCC 23355 | 0 | 0 | 0 | 3+ | 3+ | 4+ | 4+ | 4+ | 500 |
| *Pseudomonas aeruginosa* ATCC 9027 | 0 | 0 | 1+ | 3+ | 4+ | 4+ | 4+ | 4+ | 1000 |
| *Pseudomonas aeruginosa* ATCC 15442 | 0 | 0 | 4+ | 4+ | 4+ | 4+ | 4+ | 4+ | 1000 |
| *Pseudomonas aeruginosa* ATCC 13388 | 0 | 0 | 1+ | 4+ | 4+ | 4+ | 4+ | 4+ | 1000 |
| *Pseudomonas stutzeri* | 0 | 0 | 0 | 3+ | 4+ | 4+ | 4+ | 4+ | 500 |
| *Candida albicans* ATCC 10231 | 0 | 0 | 0 | 0 | 0 | 2+ | 4+ | 4+ | 125 |
| *Saccharomyces cerevisiae* | 0 | 0 | 0 | 0 | 0 | 0 | 0 | 4+ | 32 |
| *Aspergillus niger* ATCC 9642 | 0 | 0 | 0 | 0 | 1+ | 4+ | 4+ | 4+ | 250 |
| *Pencillium chrysogenum* ATCC 9480 | 0 | 0 | 0 | 0 | 0 | 1+ | 3+ | 4+ | 125 |
| *Trichophyton mentagrophytes* | 0 | 0 | 0 | 0 | 0 | 0 | 0 | 4+ | <32 |

Thus, the antimicrobial activity was greater than that of the composition tested in Example 15 since more of the eutectic oil solution was incorporated into the test media.

EXAMPLE 17

Example 1 was repeated using 5 g of a eutectic mixture of isopropyl p-hydroxybenzoate, sec-butyl p-hydroxybenzoate and amyl p-hydroxybenzoate in a ratio of 4:1.8:4.8, 39 g of the "Glydant" solution and 1.7 g (3.7%) of sodium lauryl sulfate. This produced a clear solution.

EXAMPLE 18

Example 17 was repeated using 15 g of the eutectic mixture, 13 g of the "Glydant" solution and approximately 3 g (9.1%) of sodium lauryl sulfate. This produced a clear solution.

EXAMPLE 19

Example 1 was repeated using 5 g of a eutectic mixture of sec-butyl p-hydroxybenzoate, isobutyl p-hydroxybenzoate and n-butyl p-hydroxybenzoate in a ratio of 2.3:4:2.83 39 g of the "Glydant" solution and 1 g (2.2%) of sodium lauryl sulfate. This produced a clear solution.

EXAMPLE 20

Example 19 was repeated using 25 g of the eutectic mixture, 21.5 g of the "Glydant" solution and 5 g (9.7%) of sodium lauryl sulfate. This produced a clear solution.

In view of the above, it will be seen that the several objects of the invention are achieved and other advantageous results attained.

As many changes could be made in the above products and methods without departing from the scope of the invention, it is intended that all matter contained in the above description shall be interpreted as illustrative and not in a limiting sense.

We claim:

1. A freeze and heat stable composition having broad spectrum antimicrobial activity consisting of a clear solution containing approximately 10% to 90% by weight of a eutectic mixture of three or more lower alkyl esters of p-hydroxybenzoic acid, approximately 10% to 90% by weight of a solution containing 55% of 1,3-bis(hydroxymethyl)-5,5-dimethylhydantoin and 45% of water, and approximately 0.5% to 10% by weight based on the weight of said eutectic mixture and said 1,3-bis(hydroxymethyl)-5,5-dimethylhydantoin solution of an anionic surfactant.

2. A composition as set forth in claim 1 wherein said anionic surfactant is selected from the group consisting of dioctyl sodium sulfosuccinate, sodium lauryl sulfate and the ammonium or sodium salt of sulfated nonylphenoxypoly(ethyleneoxy) ethanol.

3. A composition as set forth in claim 1 wherein said clear solution contains approximately 90% by weight of said eutectic mixture, approximately 10% by weight of said 1,3-bis(hydroxymethyl)-5,5-dimethylhydantoin solution and approximately 6% by weight of dioctyl sodium sulfosuccinate based on the weight of said eutectic mixture and said 1,3-bis(hydroxymethyl)-5,5-dimethylhydantoin solution.

4. A composition as set forth in claim 1 wherein said clear solution contains approximately 55% by weight of said eutectic mixture, approximately 45% by weight of said 1,3-bis(hydroxymethyl)-5,5-dimethylhydantoin solution and approximately 7% by weight of sodium lauryl sulfate based on the weight of said eutectic mixture and said 1,3-bis(hydroxymethyl)-5,5-dimethylhydantoin solution.

5. A composition as set forth in claim 1 wherein said clear solution contains aproximately 50% by weight of said eutectic mixture, approximately 50% by weight of said 1,3-bis(hydroxymethyl)-5,5-dimethylhydantoin solution and approximately 10% by weight of dioctyl sodium sulfosuccinate based on the weight of said eutectic mixture and said 1,3-bis(hydroxymethyl)-5,5-dimethylhydantoin solution.

6. A composition as set forth in claim 1 wherein said clear solution contains approximately 40% by weight of said eutectic mixture, approximately 60% by weight of said 1,3-bis(hydroxymethyl)-5,5-dimethylhydantoin solution and approximately 5% by weight of the ammonium salt of sulfated nonylphenoxypoly(ethyleneoxy) ethanol based on the weight of said eutectic mixture and said 1,3-bis(hydroxymethyl)-5,5-dimethylhydantoin solution.

7. A composition as set forth in claim 1 wherein said clear solution contains approximately 10% by weight of said eutectic mixture, approximately 90% by weight of said 1,3-bis(hydroxymethyl)-5,5-dimethylhydantoin solution and approximately 2% by weight of the ammonium salt of sulfated nonylphenoxypoly(ethyleneoxy) ethanol based on the weight of said eutectic mixture and said 1,3-bis(hydroxymethyl)-5,5-dimethylhydantoin solution.

8. A composition as set forth in claim 1 wherein said clear solution contains between approximately 2% and 10% by weight of said anionic surfactant based on the weight of said eutectic mixture and said 1,3-bis(hydroxymethyl)-5,5-dimethylhydantoin solution.

9. A freeze and heat stable composition having broad spectrum antimicrobial activity consisting of a clear solution containing approximately 10% to 90% by weight of a eutectic mixture of isopropyl p-hydroxybenzoate, isobutyl p-hydroxybenzoate and n-butyl p-hydroxybenzoate in a ratio between approximately 1:1:1 and 4:2:2, respectively, approximately 10% to 90% by weight of a solution containing approximately 55% of 1,3-bis(hydroxymethyl)-5,5-dimethylhydantoin and 45% of water, and approximately 0.5% to 10% by weight based on the weight of said eutectic mixture and said 1,3-bis(hydroxymethyl)-5,5-dimethylhydantoin solution of an anionic surfactant.

10. A composition as set forth in claim 9 wherein said anionic surfactant is selected from the group consisting of dioctyl sodium sulfosuccinate, sodium lauryl sulfate and the ammonium or sodium salt of sulfated nonylphenoxypoly(ethyleneoxy) ethanol.

11. A composition as set forth in claim 9 wherein said eutectic mixture of isopropyl p-hydroxybenzoate, isobutyl p-hydroxybenzoate and n-butyl p-hydroxybenzoate has a ratio of 4:2.5:2.5, respectively.

12. A composition as set forth in claim 9 wherein said clear solution contains approximately 90% by weight of said eutectic mixture, approximately 10% by weight of said 1,3-bis(hydroxymethyl)-5,5-dimethylhydantoin solution and approximately 6% by weight of dioctyl sodium sulfosuccinate based on the weight of said eutectic mixture and said 1,3-bis(hydroxymethyl)-5,5-dimethylhydantoin solution.

13. A composition as set forth in claim 9 wherein said clear solution contains approximately 55% by weight of said eutectic mixture, approximately 45% by weight of said 1,3-bis(hydroxymethyl)-5,5-dimethylhydantoin solution and approximately 7% by weight of sodium lauryl sulfate based on the weight of said eutectic mixture and said 1,3-bis(hydroxymethyl)-5,5-dimethylhydantoin solution.

14. A composition as set forth in claim 9 wherein said clear solution contains approximately 50% by weight of said eutectic mixture, approximately 50% by weight of said 1,3-bis(hydroxymethyl)-5,5-dimethylhydantoin solution and approximately 10% by weight of dioctyl sodium sulfosuccinate based on the weight of said eutectic mixture and said 1,3-bis(hydroxymethyl)-5,5-dimethylhydantoin solution.

15. A composition as set forth in claim 9 wherein said clear solution contains approximately 40% by weight of said eutectic mixture, approximately 60% by weight of said 1,3-bis(hydroxymethyl)-5,5-dimethylhydantoin solution and approximately 5% by weight of the ammonium salt of sulfated nonylphenoxypoly(ethyleneoxy) ethanol based on the weight of said eutectic mixture and said 1,3-bis(hydroxymethyl)-5,5-dimethylhydantoin solution.

16. A composition as set forth in claim 9 wherein said clear solution contains approximately 10% by weight of said eutectic mixture, approximately 90% by weight of said 1,3-bis(hydroxymethyl)-5,5-dimethylhydantoin solution and approximately 2% by weight of the ammonium salt of sulfated nonylphenoxypoly(ethyleneoxy) ethanol based on the weight of said eutectic mixture and said 1,3-bis(hydroxymethyl)-5,5-dimethylhydantoin solution.

17. A composition as set forth in claim 9 wherein said clear solution contains between approximately 2% and 10% by weight of said anionic surfactant based on the weight of said eutectic mixture and said 1,3-bis(hydroxymethyl)-5,5-dimethylhydantoin solution.

18. A method of inhibiting antimicrocrobial activity of a microoganism selected from the group consisting of bacteria, yeast and fungi comprising contacting said microorganism with a freeze and heat stable composition consisting of a clear solution containing approximately 10% to 90% by weight of a eutectic mixture of three or more lower alkyl esters of p-hydroxybenzoic acid, approximately 10% to 90% by weight of a solution containing approximately 55% of 1,3-bis(hydroxymethyl)-5,5-dimethylhydantoin and 45% of water, and approximately 0.5% to 10% by weight based on the weight of said eutectic mixture and said 1,3-bis(hydroxymethyl)-5,5-dimethylhydantoin solution of an anionic surfactant.

19. A method as set forth in claim 18 wherein said anionic surfactant is selected from the group consisting of dioctyl sodium sulfosuccinate, sodium lauryl sulfate and the ammonium or sodium salt of sulfated nonylphenoxypoly(ethyleneoxy) ethanol.

20. A method as set forth in claim 18 wherein said clear solution contains approximately 90% by weight of said eutectic mixture, approximately 10% by weight of said 1,3-bis(hydroxymethyl)-5,5-dimethylhydantoin solution and approximately 6% by weight of dioctyl sodium sulfosuccinate based on the weight of said eutectic mixture and said 1,3-bis(hydroxymethyl)-5,5-dimethylhydantoin solution.

21. A method as set forth in claim 18 wherein said clear solution contains approximately 55% by weight of said eutectic mixture, approximately 45% by weight of said 1,3-bis(hydroxymethyl)-5,5-dimethylhydantoin solution and approximately 7% by weight of sodium lauryl sulfate based on the weight of said eutectic mixture and said 1,3-bis(hydroxymethyl)-5,5-dimethylhydantoin solution.

22. A method as set forth in claim 20 wherein said clear solution contains approximately 50% by weight of said eutectic mixture, approximately 50% by weight of said 1,3-bis(hydroxymethyl)-5,5-dimethylhydantoin solution and approximately 10% by weight of dioctyl sodium sulfosuccinate based on the weight of said eutectic mixture and said 1,3-bis(hydroxymethyl)-5,5-dimethylhydantoin solution.

23. A method as set forth in claim 20 wherein said clear solution contains approximately 40% by weight of said eutectic mixture, approximately 60% by weight of said 1,3-bis(hydroxymethyl)-5,5-dimethylhydantoin solution and approximately 5% by weight of the ammonium salt of sulfated nonylphenoxypoly(ethyleneoxy) ethanol based on the weight of said eutectic mixture and said 1,3-bis(hydroxymethyl)-5,5-dimethylhydantoin solution.

24. A method as set forth in claim 18 wherein said clear solution contains approximately 10% by weight of said eutectic mixture, approximately 90% by weight of said 1,3-bis(hydroxymethyl)-5,5-dimethylhydantoin solution and approximately 2% by weight of the ammonium salt of sulfated nonylphenoxypoly(ethyleneoxy)

ethanol based on the weight of said eutectic mixture and said 1,3-bis(hydroxymethyl)-5,5-dimethylhydantoin solution.

25. A method as set forth in claim 18 wherein said clear solution contains between approximately 2% and 10% by weight of said anionic surfactant based on the weight of said eutectic mixture and said 1,3-bis(hydroxymethyl)-5,5-dimethylhydantoin solution.

26. A method as set forth in claim 18 wherein the minimum inhibitory concentration of said composition contacting said microorganism ranges between 32 ppm and 2000 ppm.

27. A method of inhibiting antimicrobial activity of a microorganism selected from the group consisting of bacteria, yeast and fungi comprising contacting said microorganism with a freeze and heat stable composition consisting of a clear solution containing approximately 10% to 90% by weight of a eutectic mixture of isopropyl p-hydroxybenzoate, isobutyl p-hydroxybenzoate and n-butyl p-hydroxybenzoate in a ratio between approximately 1:1:1 and 4:2:2, respectively, approximately 10% to 90% by weight of a solution containing approximately 55% of 1,3-bis(hydroxymethyl)-5,5-dimethylhydantoin and 45% of water, and approximately 0.5% to 10% by weight based on the weight of said eutectic mixture and said 1,3-bis(hydroxymethyl)-5,5-dimethylhydantoin solution of an anionic surfactant.

28. A method as set forth in claim 27 wherein said anionic surfactant is selected from the group consisting of dioctyl sodium sulfosuccinate, sodium lauryl sulfate and the ammonium or sodium salt of sulfated nonylphenoxypoly(ethyleneoxy) ethanol.

29. A method as set forth in claim 27 wherein said eutectic mixture of isopropyl p-hydroxybenzoate, isobutyl p-hydroxybenzoate and n-butyl p-hydroxybenzoate has a ratio of 4:2.5:2.5, respectively.

30. A method as set forth in claim 27 wherein said clear solution contains approximately 90% by weight of said eutectic mixture, approximately 10% by weight of said 1,3-bis(hydroxymethyl)-5,5-dimethylhydantoin solution and approximately 6% by weight of dioctyl sodium sulfosuccinate based on the weight of said eutectic mixture and said 1,3-bis(hydroxymethyl)-5,5-dimethylhydantoin solution.

31. A method as set forth in claim 27 wherein said clear solution contains approximately 55% by weight of said eutectic mixture, approximately 45% by weight of said 1,3-bis(hydroxymethyl)-5,5-dimethylhydantoin solution and approximately 7% by weight of sodium lauryl sulfate based on the weight of said eutectic mixture and said 1,3-bis(hydroxymethyl)-5,5-dimethylhydantoin solution.

32. A method as set forth in claim 27 wherein said clear solution contains approximately 50% by weight of said eutectic mixture, approximately 50% by weight of said 1,3-bis(hydroxymethyl)-5,5-dimethylhydantoin solution and approximately 10% by weight of dioctyl sodium sulfosuccinate based on the weight of said eutectic mixture and said 1,3-bis(hydroxymethyl)-5,5-dimethylhydantoin solution.

33. A method as set forth in claim 27 wherein said clear solution contains approximately 40% by weight of said eutectic mixture, approximately 60% by weight of said 1,3-bis(hydroxymethyl)-5,5-dimethylhydantion solution and approximately 5% by weight of the ammonium salt of sulfated nonylphenoxypoly(ethyleneoxy) ethanol based on the weight of said eutectic mixture and said 1,3-bis(hydroxymethyl)-5,5-dimethylhydantoin solution.

34. A method as set forth in claim 27 wherein said clear solution contains approximately 10% by weight of said eutectic mixture, approximately 90% by weight of said 1,3-bis(hydroxymethyl)-5,5-dimethylhydantoin solution and approximately 2% by weight of the ammonium salt of sulfated nonylphenoxypoly(ethyleneoxy) ethanol based on the weight of said eutectic mixture and said 1,3-bis(hydroxymethyl)-5,5-dimethylhydantoin solution.

35. A method as set forth in claim 27 wherein said clear solution contains between approximately 2% and 10% by weight of said anionic surfactant based on the weight of said eutectic mixture and said 1,3-bis(hydroxymethyl)-5,5-dimethylhydantoin solution.

36. A method as set forth in claim 27 wherein the minimum inhibitory concentration of said composition contacting said microorganism ranges between 32 ppm and 2000 ppm.

* * * * *